United States Patent [19]

Takahashi

[11] Patent Number: 4,982,105

[45] Date of Patent: Jan. 1, 1991

[54] SURFACE INSPECTING APPARATUS WITH STRIP WIDTH DIVIDING MEANS

[75] Inventor: Ippei Takahashi, Shizouka, Japan

[73] Assignee: Fuji Photo Film Co., Ltd., Kanagawa, Japan

[21] Appl. No.: 326,502

[22] Filed: Mar. 20, 1989

[30] Foreign Application Priority Data

Mar. 18, 1988 [JP] Japan ................................ 63-65338

[51] Int. Cl.[5] ............................................ G01N 21/88

[52] U.S. Cl. ...................................... 259/563; 356/431

[58] Field of Search ............... 250/562, 563, 571, 572; 356/430, 431

[56] References Cited

U.S. PATENT DOCUMENTS

| | | | |
|---|---|---|---|
| 3,618,063 | 11/1971 | Johnson | 356/431 |
| 3,898,469 | 8/1975 | Nichols et al. | 250/563 |
| 4,134,684 | 1/1979 | Jette | 250/563 |
| 4,546,444 | 10/1985 | Bullis | 356/431 |
| 4,581,632 | 4/1986 | Davis et al. | 250/572 |
| 4,868,403 | 9/1989 | Takahashi et al. | 250/563 |

*Primary Examiner*—David C. Nelms

*Attorney, Agent, or Firm*—Young & Thompson

[57] ABSTRACT

An apparatus for inspecting the surface of a web material moving lengthwise at a constant speed by scanning the surface in the direction of the width of the surface with a light beam. The scanned beam modulated by the surface is received and converted into an electric signal which is divided into division signals representing lengthwise areas of the surface. At least one of the lengthwise areas or lanes into which the surface is divided is specified to be subjected to surface inspection. Surface signals of the specified lengthwise areas or lanes are separated from the other surface signals and evaluated for qualifying the surface of the web material.

5 Claims, 5 Drawing Sheets

FIG. 6A
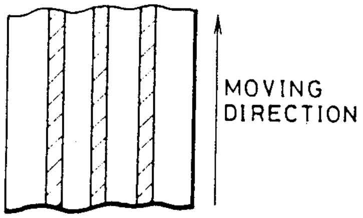
FIG. 6B
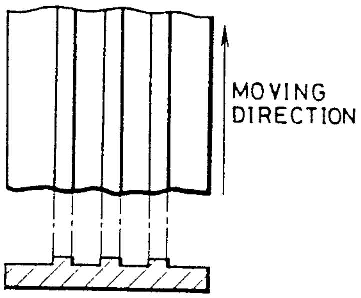
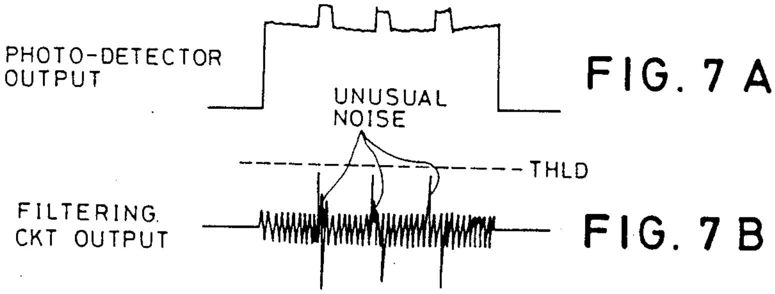
FIG. 7A
FIG. 7B
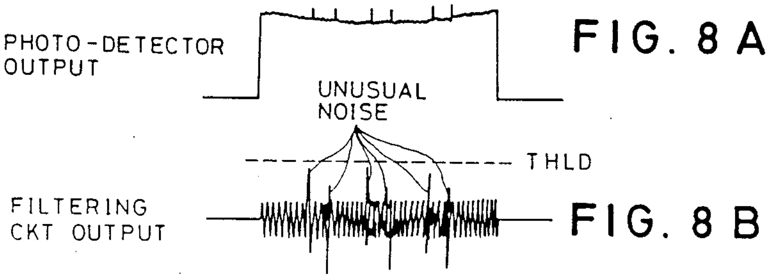
FIG. 8A
FIG. 8B
MOVING DIRECTION
MOVING DIRECTION
PHOTO-DETECTOR OUTPUT
UNUSUAL NOISE
FILTERING CKT OUTPUT
THLD
PHOTO-DETECTOR OUTPUT
UNUSUAL NOISE
FILTERING CKT OUTPUT
THLD

SURFACE INSPECTING APPARATUS WITH STRIP WIDTH DIVIDING MEANS

BACKGROUND OF THE INVENTION

The present invention relates to a surface inspecting apparatus for transversely scanning the surface of a web material continuously moving lengthwise to detect surface defects of the web material so as to qualify or evaluate the surface condition of the web material.

Various apparatus are well known for scanning a surface of a continuously moving web material, such as films, paper sheet, thin plates or the like, with a scanning beam in the direction of the width of the web material to detect surface defects of the web material for evaluating or qualifying the web material. Some of these surface scanning apparatus utilize a photo-electric detector which detects light modulated by surface defects of the web material to provide surface defect signals. Based on the surface defect signals a judgment is made as to whether the web material has unacceptable surface defects. Because they are non-contact devices and permit high speed surface defect detection, these surface inspection apparatus can be widely used in a web material production line.

One such surface inspection apparatus utilizes a filtering circuit for filtering out noises included in detected surface signals, the filtered surface signals being sent to a binary signal generating circuit. The binary signal generating circuit compares the surface signal with a predetermined threshold level (THLD) to transform it into a binary signal.

Surface signals modulated by a web material having a surface pattern non-uniform or irregular in the transverse direction of the web material often contain unusual noises regularly generated during repeated transverse scans. Therefore, the threshold level should be higher than a maximum level of such regularly generated unusual noises which is relatively high. Therefore, only surface defects which provide defect signals having signal levels higher than the threshold level can be detected.

OBJECTS OF THE INVENTION

It is, therefore, a primary object of the present invention to provide a surface inspection apparatus which can detect surface defects of a web material continuously moving in the lengthwise direction of the web material with a desired level of acuity of inspection.

It is another object of the present invention to provide a surface inspection apparatus which can detect surface defects of a web material continuously moving in the lengthwise direction of the web material which has a surface pattern which is uniform in the lengthwise direction of the we material but irregular in the transverse direction.

SUMMARY OF THE INVENTION

The above objects of the present invention are achieved by a surface inspection apparatus for inspecting a surface of a web material running in a lengthwise direction by repeatedly scanning the surface in the direction of the width of the web material with a light beam, such as a laser beam, the surface modulating the light beam. The surface inspecting apparatus comprises surface signal detecting means for detecting modulated light reflected from the web material as surface signals, dividing means for dividing the width of the web material into a plurality of transverse portions for each transverse scan so as to define a plurality of lengthwise areas or lanes constituting the transverse portions, respectively, specifying means for specifying at least one of the lengthwise areas or lanes to be subjected to inspection, and inspecting means for separating surface signals of only the specified lengthwise areas or lanes from the surface signals from the surface signal detecting means to evaluate the separated surface signals for qualifying the surface of the web material.

According to the surface inspection apparatus in accordance with a preferred embodiment of the present invention, the inspecting means includes binary signal generating means. The binary signal generating means transforms the separated surface signals into binary signals by comparing them with a predetermined threshold value which is variable according to inspection acuity levels. Qualifying the surface of the web is carried out by evaluating the binary surface signals.

According to the surface inspection apparatus in accordance with another preferred embodiment of the present invention, the apparatus includes at least two inspecting means. Each inspecting means includes the binary signal generating means. The threshold values of the two binary signal generating means are different from each other.

The surface of the web material is divided into a plurality of lengthwise areas or lanes. A lane or lanes including regular surface patterns extending lengthwise is excluded from web surface inspection or qualification. In other words, at least one lane is effectively subjected to inspection for surface qualification. The lane specification or lane exclusion enables avoiding false surface defect signals generated by the regular surface pattern for accurate surface inspection.

BRIEF DESCRIPTION OF THE DRAWINGS

This invention will be described with reference to its embodiments shown in the accompanying drawings wherein:

FIGS. 6A and 6B are plan views showing fragments of the surfaces of web materials with regular pattern surfaces to be scanned;

FIGS. 7A and 7B show waveforms of signals produced by the surface shown in FIGS. 6A and provided from various elements of FIG. 3; and FIGS. 8A and 8B show waveforms of signals produced by the surface shown in FIG. 6B and provided from various elements of FIG. 3.

DETAILED DESCRIPTION OF THE INVENTION

Before describing the present invention in detail, reference is made to FIGS. 6A, 6B, 7 and 8 for the purpose of providing a brief background that will enhance an understanding of the surface signals generated by web materials with substantially regular surface patterns. Referring to FIG. 6A, a surface of a web material to be inspected is shown, having a surface pattern including portions continuously extending in the lengthwise direction wherein the web material runs for surface inspection. Scanning light reflected and modulated by such a surface is converted to a photoelectric output shown in FIG. 7A. The photo-electric output is filtered, providing the surface signals shown in FIG. 7B.

FIG. 6B shows a surface of another web material having an uneven surface of which the pattern extends regularly in the lengthwise direction or web running direction. Similarly, scanning light reflected and modulated by such a surface is converted to the photo-electric output shown in FIG. 8A and the photo-electric output is filtered, providing the surface signals shown in FIG. 8B.

In any case, the surface signals regularly include unusual noise produced depending on the surface pattern. For excluding such unusual noise for surface inspection, a threshold level or value for evaluating the surface signals should be set to a level higher than the maximum level of the unusual noise, as shown by a chained line in FIGS. 7B and 8B. Therefore, only surface signals produced by surface defects, which are higher than the threshold level, can be effectively utilized for surface evaluation, whereby the level of acuity or accuracy of the surface inspection will be greatly lowered.

Figure 1:
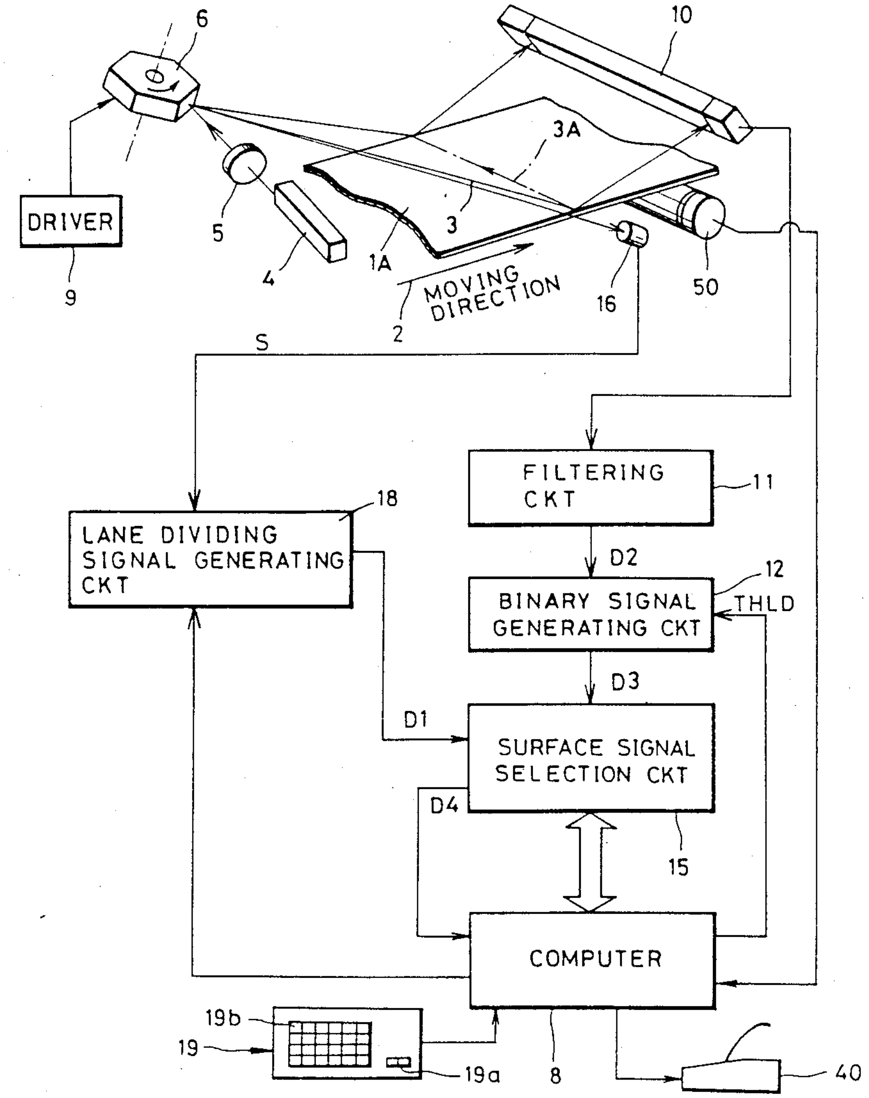
FIG. 1 is a diagrammatical illustration showing a surface inspection apparatus in accordance with a preferred embodiment of the present invention.

Referring now to FIG. 1, showing a surface inspection apparatus in accordance with a preferred embodiment of the present invention, a web material 1A to be subjected to surface defect inspection is continuously moved or transported lengthwise, in a direction shown by an arrow 2, at a constant speed of movement. While the web material 1A moves lengthwise, a laser beam 3 scans the upper surface of the web material 1A transversely, in the direction of the width of the web material 1A, from the right to the left as viewed in FIG. 1. The laser beam 3, which is emitted by a laser radiation source 4, is reflected by one of the mirror surfaces of a polyhedral mirror 6 rotating in a counterclockwise direction at a constant speed and is focussed on the upper surface of the web material 1A by a focusing lens 5. The laser beam 3 moves along a transverse path 3A on the web material 1A, as a result of the counterclockwise rotation of the polyhedral mirror 6 which is caused by a driver 9.

Figure 2:
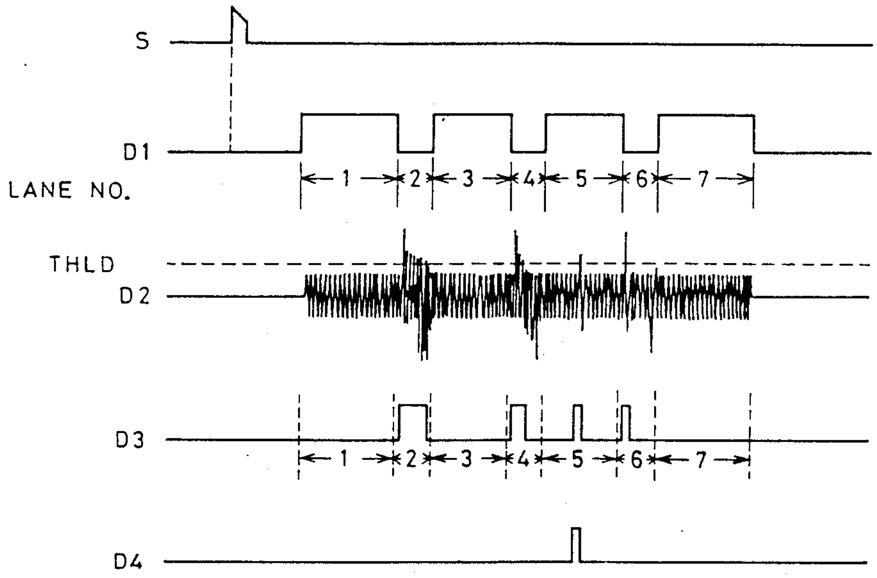
FIG. 2 shows waveforms of signals provided from various elements of FIG. 1.

A photo-detector 10 is disposed above the web material 1A and extends perpendicular to the lengthwise direction of the web material 1A to receive the laser beam 3 modulated in intensity and reflected by the upper surface of the web material lA, and outputs electric outputs as surface signals. The surface signal output from the photo-detector 10 is proportional in level to the intensity of the reflected laser beam 3 received thereby and is sent to a filtering circuit 11 for filtering out DC noise components therefrom so as to provide an available surface signal D2 as shown in FIG. 2. The surface signal D2 is then transmitted to a binary signal generating circuit 12 for providing a binary surface signal D3 of "H" level indicating that there is a critical surface defect in the surface of the web material 1A only when the surface signal D2 is higher than a predetermined threshold level (THLD). The threshold level (THLD) can be appropriately changed by means of an adjusting key 19a of a keyboard 19.

If the web material 1A has a surface pattern that does not change in the direction of movement thereof as is shown in FIG. 6A, it suffices to divide the surface of the web material 1A to be scanned into several surface portions or lanes, for example, surface lanes Nos. 1 to 7 as shown in FIG. 2, for each transverse scan of the web material lA. During a single transverse scan of the web material 1A, if there is no irregular noise for the Nos. 1, 3, 5 and 7 surface lanes, all output signals from the photo-detector 10 for those lanes are effectively used to evaluate the surface of the web material 1A. The surface lanes for which surface signals can be effectively used to evaluate the surface condition of the web material 1A are designated through numerical keys 19b of the keyboard 19.

Similarly, if the web material lA has a surface which is uneven in the direction of the width thereof but that does not change in the direction of movement thereof as is shown in FIG. 6B, the surface lanes for which surface signals can be effectively used to evaluate the surface condition of the web material 1A are designated through numerical keys 19b of the keyboard 19.

A photo-detector 16 is disposed out of the path of movement of the web material 1A for detecting the laser beam 3 at a reference starting position from which a transverse scan starts. When the photo-detector 16 detects the laser beam 3, it produces a trigger signal S shown in FIG. 2 which actuates a lane dividing signal generating circuit 18 after a certain time from the production of the trigger signal S. This certain time is determined correspondingly to the time necessary for the laser beam 3 to travel between the photodetector 16 and the side edge of the web material 1A. The lane dividing signal generating circuit 18 generates a surface lane indicating signal D1 in synchronism with the rotation of the polyhedral mirror 6 which is in turn sent to a surface signal selection circuit 15. The surface lane indicating signal D1, as is shown in FIG. 2, comprises a signal in the form of a rectangular pulse of a predetermined high level "H" for defining the designated web surface portions of the web material 1A and designates the web surface portions to be effectively scanned to detect surface defects.

The surface signal selection circuit 15 responds to the binary surface signals D3 from the binary signal generating circuit 12 only during the presence of the high level surface lane indicating signal D1 from the lane dividing signal generating circuit 18. That is, when the binary surface signal D3 provided from the binary signal generating circuit 12 is of the high level "H", the surface signal selecting circuit 15 correspondingly provides a computer 8 with a high level (H) of an evaluation signal D4.

The computer 8 evaluates the distribution of surface defects of the indicated or selected surface lanes by utilizing the evaluation signals D4 from the surface signal selecting circuit 15.

An encoder 50 disposed below the path of the web material 1A generates line speed pulses indicating the length of movement of the web material 1A in the lengthwise moving direction 2, which are transmitted to the computer 8. With reference to the line speed pulses, the computer 8 detects a predetermined number of data bits, namely a predetermined unit length of movement, of the web material 1A to be inspected. The results of this surface defect evaluation and data on the position of the data bits of the web material 1A are printed out by means of a printer 40.

The operation of the surface inspection apparatus thus constructed will be described in detail with reference to FIG. 2. If the web material 1A has a stripe-patterned surface as shown in FIG. 6A, the web material 1A is divided into, for example in this embodiment, seven surface lanes, Nos. 1 to 7; and surface signals from the Nos 1, 3, 5 and 7 lanes are effectively utilized. Instructions for dividing the web material 1A and selectively indicating the Nos. 1, 3, 5 and 7 lanes are entered via the keyboard 19 and sent to the lane signal generating circuit 18 by the computer 8. The instructions are stored in a memory in the lane signal generating circuit 18.

The driver 9 causes the rotation of the polyhedral mirror 6 and the laser radiation source 4 is excited, which initiates the transverse scanning of the upper surface of the web material 1A. When the photo-detector 16 detects the laser beam 3 at the reference starting position, it provides the lane signal generating circuit 18 with the trigger signal S. After a predetermined time period from the reception of the trigger signal S, the lane signal generating circuit 18 supplies the lane specifying signals D1 to the surface signal selecting circuit 15 according to the instructions provided from the computer 8 and stored in the memory thereof.

The laser beam 3 is modulated and reflected by the upper surface of the web material 1A moving in the lengthwise direction at a constant speed, and the reflected laser beam 3 is detected by the photo-detector 10. The photo-detector 10 generates a photo-electric signal as a surface signal of which the signal level is proportional to the intensity of the modulated laser beam reflected by the upper surface of the web material 1A. The filtering circuit 11 filters out noise from the surface signals from the photo-detector 10, and the filtered surface signals D2 are sent to the binary signal generator 12. If the surface signal D2 is higher than the predetermined threshold level THLD, the binary signal generator 12 outputs or provides the surface signal selecting circuit 15 with a binary surface defect signal D3 of "H" level.

When the binary surface signal D3 is of "H" level while a surface lane specifying signal D1 of "H" level is continuously provided, the surface signal selection circuit 15 outputs a surface evaluation signal D4 of "H" level and sends it to the computer 8.

Based on the surface evaluation signals D4 of "H" level for several transverse scans, the computer 8 evaluates the distribution of surface defects of the selected surface lane or lanes. The result of this evaluation and the position data of the scanned data cell are printed out by the printer 40. It is to be noted that the level of surface defect inspection can be changed by changing the threshold level THLD by an adjusting key 19*a* of the keyboard 19. Part of the web material 1A corresponding to the data bit or bits evaluated to include surface defects is determined to be substandard.

Figure 3:
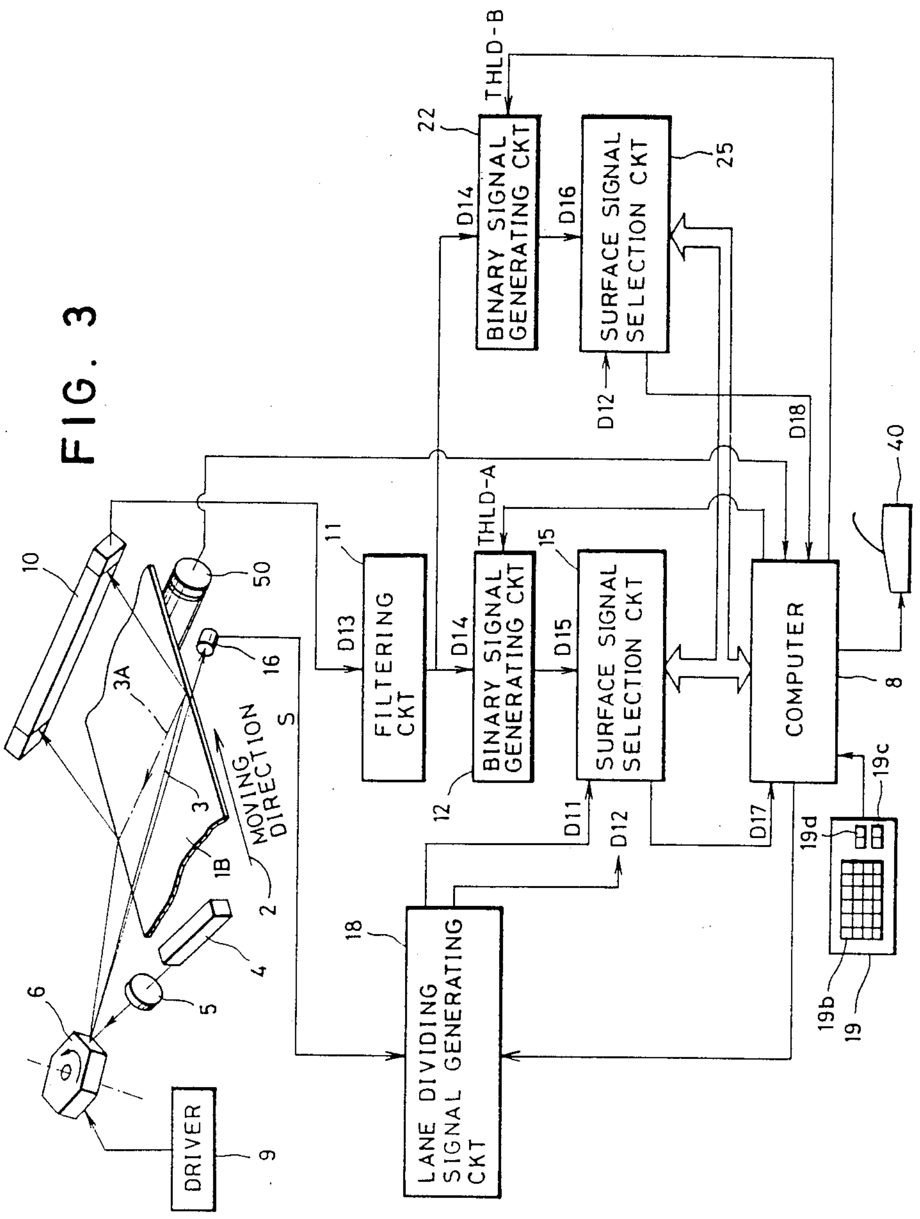
FIG. 3 is a diagrammatical illustration showing a surface inspection apparatus in accordance with another preferred embodiment of the present invention.
Figure 4:
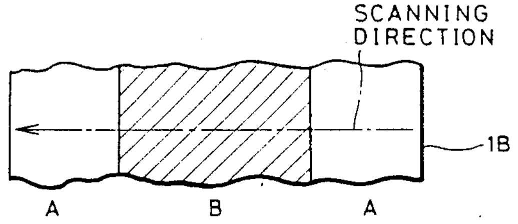
FIG. 4 is a plan view showing a fragment of the surface of a web material with a regular pattern surface to be scanned.
Figure 5:
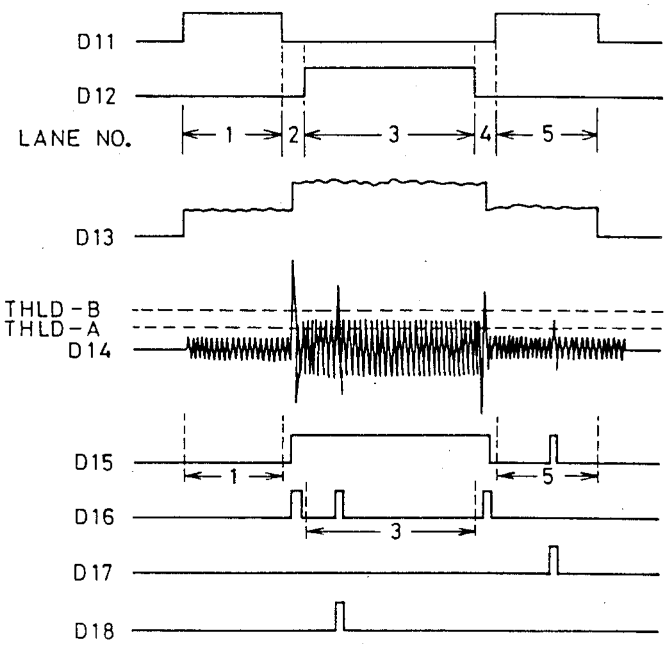
FIG. 5 shows waveforms of signals provided from various elements of FIG. 3.

Referring to FIGS. 3 to 5, a surface inspection apparatus in accordance with another preferred embodiment of the present invention is shown, including another binary signal generating circuit 22 and surface signal selection circuit 25. This embodiment is advantageously used to inspect a web material 1B having a surface pattern illustrated in FIG. 4, namely, the upper surface of the web material 1B has a plurality of surface areas A and B that are relatively wide in the transverse direction. Specifically, the upper surface of the web material 1B has a central surface area B and side surface areas A on both sides of the surface area B. The surface areas A and B are different from the normal surface conditions.

As is shown in FIG. 5, the filtered surface signals D14 from the filtering circuit 11 include noises modulated by the surface areas A and B having different surface conditions, respectively, which are not always of the same level. To distinguish defects of the surface areas A and B from each other the optimum threshold levels should be different for the surface areas A and B. In addition to this, since unusual noise will be regularly generated at each boundary between the surface areas A and B for each single transverse scan, it is necessary to utilize surface signals modulated by a selected surface lane or lanes in the same manner as for the web material 1A having a stripe-patterned surface. For this reason, the upper surface of the web material 1B should be divided into, for example, five lanes, Nos. 1 to 5, for each single transverse scan, by utilizing the lane specifying signals D11 and D12 generated by the lane signal generating circuit 18 as shown in FIG. 5, correspondingly to the surface pattern shown in FIG. 4 of the web material 1B. The specifying of a surface lane is performed via the numerical key 19*b* of the keyboard 19. In addition to the specifying of the surface lane, instructions are entered in order to utilize surface signals of the No. 1 and No. 5 surface lanes for the surface areas A excluding the boundaries and surface defect signals of the No. 3 surface lane for the surface area B excluding the boundaries. The optimum threshold levels THLD-A and THLD-B for the surface areas A and B, respectively, can be suitably independently changed by an adjusting key 19*c* of the keyboard 19.

The filtered surface signals D14 from the filtering circuit 11 are sent to the binary signal generating circuit 12 to be compared with the threshold level THLD-A to provide binary surface signals of "H" level D15 when higher than the threshold level THLD-A. The filtered surface signals D14 are also sent to the binary signal generating circuit 12 to be compared with the threshold level THLD-B to provide binary surface signals of "H" level D16 when higher than the threshold level THLD-B. The binary surface signals D15 and D16 are then sent to the surface signal selection circuits 15 and 25, respectively. The lane signal generating circuit 18 provides the surface signal selection circuit 15 with No. 1 and No. 5 lane specifying signals of "H" level D11 for selectively outputting the binary surface signals D15 of the surface areas A of the web material 1B excepting the boundaries, as evaluation signals D17. Similarly, the lane signal generating circuit 18 provides the surface signal selection circuit 25 with a No. 3 lane specifying signal D12 of "H" level for selectively outputting the binary surface signals D16 of the surface area B of the web material IB excepting the boundaries, as evaluation signals D18.

The computer 8 examines the evaluation signals D17 and D18 to evaluate the distribution of surface defects of each selected surface area A or B for surface qualification.

Although the present invention has been fully described by way of preferred embodiments thereof with reference to the accompanying drawings, it is to be noted that the possibility of making various changes and modifications will be apparent to those skilled in the art. Therefore, unless otherwise such changes and modifications depart from the true scope of the present invention, they should be construed as being included therein.

What is claimed is:

1. An apparatus for inspecting a surface of a continuously running web material by repeatedly scanning the surface in the direction of the width of said web material with a light beam, said surface modulating said light beam, said apparatus comprising:

surface signal detecting means for detecting modulated light reflected from said web material as surface signals;

dividing means for dividing the width of said web material into a plurality of transverse portions for each transverse of the light beam so as to define a plurality of lengthwise areas comprising said transverse portions;

specifying means for specifying at least one but fewer than all of said lengthwise areas to be subjected to inspection;

inspecting means for separating surfaces signals of only said specified lengthwise area from said surface signals from said surface signal detecting means to evaluate the separated surface signals; and evaluation signal generating means for generating an evaluation signal representative of only said specified lengthwise area.

2. An apparatus as defined in claim 1, wherein said inspecting means includes binary signal generating means for transforming said separated surface signals into binary signals by utilizing a predetermined threshold value to evaluate the binary surface signals for surface qualification.

3. An apparatus as defined in claim 2, wherein said threshold value is variable.

4. An apparatus as defined in claim 1, wherein said apparatus includes at least two said inspecting means each of which includes binary signal generating means for transforming said separated surface signals into binary signals by utilizing different predetermined threshold values to evaluate the binary surface signals for surface qualification.

5. An apparatus as defined in claim 4, wherein said different threshold values are independently changeable.

* * * * *